United States Patent [19]

Giordano et al.

[11] Patent Number: 5,142,093
[45] Date of Patent: Aug. 25, 1992

[54] PROCESS FOR THE PREPARATION OF 4-(2,4-DIFLUOROPHENYL)-PHENYL 4-NITRO-BENZOATE

[75] Inventors: Claudio Giordano, Monza; Laura Coppi, Florence; Maurizio Paiocchi, Milan, all of Italy

[73] Assignee: Zambon Group S.p.A., Vicenza, Italy

[21] Appl. No.: 802,398

[22] Filed: Dec. 4, 1991

[30] Foreign Application Priority Data

Dec. 19, 1990 [IT] Italy .................. 22441 A/90

[51] Int. Cl.$^5$ ........................................ C07C 205/00
[52] U.S. Cl. .................................. 560/20; 560/19
[58] Field of Search ......................................... 560/20

[56] References Cited

U.S. PATENT DOCUMENTS

| 4,216,109 | 8/1980 | Mizukuchi | 560/20 |
| 4,225,730 | 9/1980 | Jones et al. | 562/469 |
| 4,486,599 | 12/1984 | Meneghin et al. | 562/469 |

OTHER PUBLICATIONS

Merck Index, XI Ed., No. 3130, p. 495, "Diflunisal" (1983).

Primary Examiner—Jose G. Dees
Assistant Examiner—Keith MacMillan
Attorney, Agent, or Firm—Oblon, Spivak, McClelland, Maier & Neustadt

[57] ABSTRACT

A process for the preparation of 4-(2,4-difluorophenyl)-phenyl 4-nitro-benzoate, an intermediate for the preparation of 5-(2,4-difluorophenyl)-salicylic acid, which is a drug known with the international non-proprietary name Diflunisal, is described.

2 Claims, No Drawings

PROCESS FOR THE PREPARATION OF 4-(2,4-DIFLUOROPHENYL)-PHENYL 4-NITRO-BENZOATE

The present invention relates to a process for the preparation of 4-(2,4-difluorophenyl)-phenyl 4-nitro-benzoate, a compound useful for the preparation of Diflunisal.

Diflunisal is the international non-proprietary name (INN) of the compound 5-(2,4-difluorophenyl)-salicylic acid, a drug with anti-inflammatory activity (Merck Index, XI Ed., No. 3130, page 495) hereinafter indicated as compound I.

U.S. Pat. No. 4,225,730 (Merck & Co.) describes a process for the preparation of compound I comprising the preparation of 2,4-difluorobiphenyl (II), the Friedel-Crafts acylation with an acyl derivative of a $C_2-C_5$ aliphatic carboxylic acid in order to obtain a 2,4-difluorobiphenyl-4'-substituted by a $C_2-C_5$ alkylcarbonyl group, the oxidation of this compound in order to obtain a 2,4-difluorobiphenyl 4'-substituted by a $C_2-C_5$ alkylcarbonyloxy group, the hydrolysis in order to obtain 4-(2,4-difluorophenyl)-phenol (III) and the carboxylation of this latter in order to obtain compound I.

The main problems of the above process are the positional selectivity (regioselectivity) in the Friedel-Crafts reaction and the need of avoiding undesired transpositions during the oxidation.

Both these difficulties can cause the formation of by-products, even in relevant amount, with a consequent decrease in chemical yield as well as with high difficulties in the purification of the desired compound.

It is not mere chance that the only example reported in the above cited U.S. patent describes the process carried out with acetyl chloride ($C_2$-acylating agent).

In fact, it is known in the literature that a formyl derivative ($C_1$-acylating agent) is not suitable for this kind of reaction and that the increase in the carbon atom number of the acylating agent significantly increases the above problems.

Consequently, the process described in U.S. Pat. No. 4,225,730 is suitable for an industrial application only when a $C_2$-acylating agent, that is acetyl chloride, is used.

Furthermore, it is worth noting that, as far as we know, no other process having industrial applicability close to that of the process exemplified in U.S. Pat. No. 4,225,730 has never been described in the literature up to now.

In this connection, even more so, a process for the preparation of compound I comprising the acylation of compound II with a derivative of an aromatic carboxylic acid, for example a benzoic acid derivative, in order to obtain a 2,4-difluorobiphenyl 4'-substituted by a benzoyl group and the reaction of this latter according to the Baeyer-Villiger method has been never described.

Probably, the reason for that is the generally known fact that the Friedel-Crafts acylation, when carried out with an aromatic acylating agent, has a lower regioselectivity with respect to an aliphatic acylating agent and that the Baeyer-Villiger reaction, when carried out on a benzophenone derivative, gives mixtures of isomeric products caused by the formation of the ester on both the aryl groups.

We have now surprisingly found that the Friedel-Crafts acylation of compound II with 4-nitro-benzoyl chloride gives 4-(2,4-difluorophenyl)-4'-nitro-benzophenone (compound IV) with high yield and regioselectivity and that the Baeyer-Villiger reaction carried out on such a product gives 4-(2,4-difluorophenyl)-phenyl 4-nitro-benzoate (compound V) with high yield and selectivity without having practically any trace of the other isomeric ester.

Therefore, an object of the present invention is a process for the preparation of 4-(2,4-difluorophenyl)-phenyl 4-nitro-benzoate comprising the Friedel-Crafts acylation of 2,4-difluorobiphenyl with 4-nitro-benzoyl chloride in order to obtain 4-(2,4-difluorophenyl)-4'-nitro-benzophenone and the Baeyer-Villiger oxidation of this latter (scheme 1).

A second object of the present invention is a process for the preparation of 5-(2,4-difluorophenyl)-salicylic acid (Diflunisal) comprising the preparation of compound V according to the above reported process.

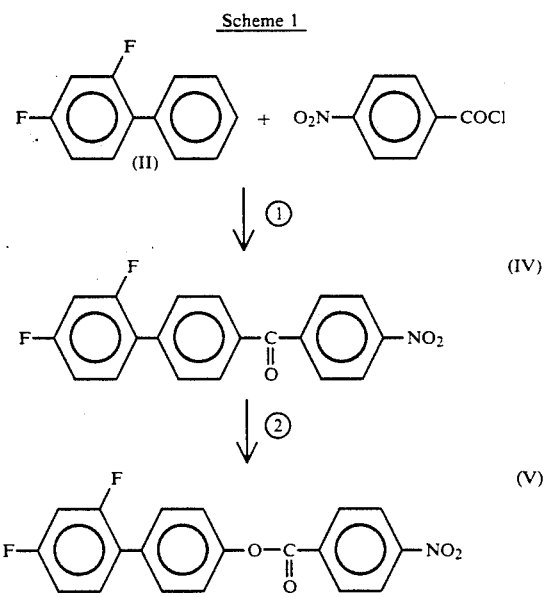

Reaction 1 in scheme 1, as already reported, is a Friedel-Crafts acylation of compound II with 4-nitro-benzoyl chloride.

The reaction conditions are those generally used in Friedel-Crafts acylations and comprise the use of a Lewis acid and of an inert solvent.

Exclusively for practical reason, it is preferred the use of $AlCl_3$ as Lewis acid. Among the suitable inert solvents aliphatic chlorinated hydrocarbons, and, in particular, methylene chloride, 1,2-dichloroethane or other solvents such as nitromethane and carbon disulfide may be cited.

The reaction is preferably carried out at a temperature from $-20°$ C. to $50°$ C., more preferably from $0°$ C. to $25°$ C.

It is worth underlining that reaction 1 must not be necessarily carried out on compound II having a high purity, but compound II can be used as a crude, that is directly from the work-up of the reaction for its preparation without any purification.

Reaction 2 in scheme 1 is a Baeyer-Villiger oxidation of the compound IV obtained from reaction 1.

The oxidation of compound IV can be carried out according to the usual experimental conditions for Baeyer-Villiger reactions.

As oxidative agent, $H_2O_2$, sodium perborate, persulfuric acid and organic peracids, optionally prepared in situ may be used. The preferred organic peracids are perbenzoic acid, mono-perphtalic acid, permaleic acid and m.chloro-perbenzoic acid.

Generally, it is preferred to carry out the reaction in the presence of a strong acid such as a sulfonic acid or a carboxylic acid which may act also as a solvent.

Alternatively, the reaction can be carried out in an inert solvent such as an aliphatic halogenated hydrocarbon or an ether.

Hydrogen peroxide ($H_2O_2$) may be also used in a basic medium, for example with sodium hydroxide, ammonium hydroxide or potassium bicarbonate so giving an already partially hydrolyzed compound.

Compounds IV and V are new and they are a further object of the invention.

The hydrolysis of compound V gives, then, 4-(2,4-difluorophenyl)phenol (III) from which compound I (Diflunisal) is obtained by carboxylation.

The hydrolysis reaction is carried out according to conventional methods.

From the hydrolysis reaction medium 4-nitro-benzoic acid is recovered and reconverted, according to conventional methods, into the corresponding acyl chloride and, then, recycled for the process of the invention.

The carboxylation of compound III is carried out according to known methods, for example according to the method described in the already cited U.S. patent or, preferably, according to the method described in U.S. Pat. No. 4,486,599 (Zambon S.p.A.).

A relevant advantage of the process object of the invention is the possibility of carrying out the carboxylation according to the method described in U.S. Pat. No. 4,486,599 directly on compound V, that is without carrying out the hydrolysis in order to transform it into compound III.

In a practical embodiment, the process of the invention comprises the acylation of 2,4-difluorobiphenyl with 4-nitro-benzoyl chloride in the presence of $AlCl_3$ in an inert solvent, particularly methylene chloride, in order to obtain compound IV and the reaction of this latter with a peracid (in particular permaleic acid or m.chloro-perbenzoic acid), with sodium perborate in the presence of an acid, for example trifluoroacetic acid, or with $H_2O_2$ and methanesulfonic acid. The obtained compound V is hydrolyzed with aqueous sodium hydroxide in order to obtain compound III and carboxylated, preferably according to the method described in U.S. Pat. No. 4,486,599.

Alternatively, compound V is directly carboxylated according to the method of U.S. Pat. No. 4,486,599.

In order to better illustrate the present invention the following examples are now given.

EXAMPLE 1

Preparation of 4-(2,4-difluorophenyl)-4'-nitro-benzophenone (compound IV)

A solution of 4-nitro-benzoyl chloride (429 g) in methylene chloride (1560 ml) was added to a mixture of aluminum trichloride (312 g) in methylene chloride (546 ml), cooled at 0° C.

A solution of 2,4-difluorobiphenyl (390 g) in methylene chloride (1300 ml) was added under stirring to the so prepared solution, kept at 0° C.

At the end of the addition, the temperature was brought to 20° C. and the reaction mixture was kept at this temperature for 18 hours. Then, the reaction mixture was poured into water and ice (4000 g) and the phases were separated.

After evaporation of the solvent under reduced pressure, isopropanol (2600 ml) was added to the resultant crude and the mixture was heated under reflux for 10 minutes. The mixtures was cooled at 5° C. and the precipitate was filtered.

Pure compound IV (488 g) was obtained.

m.p. 155°-157° C.

$^1$H-NMR (CDCl$_3$, 300 MHz) δ(ppm, TMS): 7.00 (m, 2H); 7.48 (ddd, 1H, J$_{H-F}$=8.8 Hz, J$_{H-F}$=8.8 Hz, J$_{H-H}$6.3 Hz); 7.68 (dd, AA' portion of AA'BB'system, 2H, J$_{H-H}$=8.3 Hz, J$_{H-F}$=1.6 Hz); 7.9 (d, BB' portion of AA'BB'system, 2H, J$_{H-H}$=8.3 Hz); 7.99 (d, AA' portion of AA'BB'system, 2H, J$_{H-H}$=8.7 Hz); 8.38 (d, BB' portion of AA'BB' system, 2H, J$_{H-H}$=8.7 Hz).

$^{19}$F-NMR (CDCl$_3$, 283.2 MHz) δ(ppm, CF$_3$COOH): −107.2 (m, 1F); −103.6 (m, 1F).

EXAMPLE 2

Preparation of 4-(2,4-difluorophenyl) 4'-nitro-benzophenone

Aluminum trichloride (43.7 g; 0.328 moles) was added portionwise in about 10 minutes to a mixture of 2,4-difluorobiphenyl (52.05 g; 0.274 moles) in dichloroethane (178 ml) kept at 0° C.

The temperature of the reaction mixture during the addition of aluminum trichloride arose up to 8° C.

The mixture was cooled at 0° C. and 4-nitro-benzoyl chloride (61 g; 0.328 moles) was added in about 10 minutes keeping the temperature between 0°-8° C.

At the end of the addition, the reaction mixture was kept at room temperature and kept under stirring for 20 hours.

The reaction mixture was poured into water and ice (180 g) and diluted with dichloroethane (300 ml). The mixture was heated at 55° C. and the phases were separated.

The organic phase was evaporated to residue under vacuum.

A residue (111.3 g) containing 4-(2,4-difluorophenyl)-4'-nitro-benzophenone (85.6 g) (compound IV) from HPLC analysis, was obtained. Methanol (450 ml) was added to the residue and the mixture was heated under reflux for 30 minutes, then the mixture was cooled at room temperature.

The suspension was filtered under vacuum and the solid was washed with methanol (60 ml).

Pure compound IV (85 g-91.4% yield) was obtained after drying under vacuum at 50° C. for 6 hours.

m.p. 155°-157° C.

EXAMPLE 3

Preparation of 4-(2,4-difluorophenyl)-phenyl 4-nitro-benzoate (compound V)

Sodium perborate tetrahydrate (1.5 g; 9.7 mmoles) was added to a mixture of 4-(2,4-difluorophenyl)-4'-nitro-benzophenone (1 g; 2.9 mmoles) and trifluoroacetic acid (9 ml) at 20° C., under stirring and under nitrogen for 24 hours and then poured into a mixture of methylene chloride (10 ml) and water (10 ml).

The organic phase was washed with an 8% aqueous solution of sodium bicarbonate.

After drying with sodium sulfate and evaporation of the solvent under reduced pressure, a crude (1.03 g)

containing a mixture of ester V and ketone IV in the ratio 98:2 from $^{19}$F-NMR analysis, was obtained.

The amount of ester V (0.946 g-91.9% yield) in the crude was determined by HPLC analysis.

An analytical sample (0.89 g) of the crude was crystallized from ethyl acetate giving pure compound V (0.70 g).

m.p. 149.5°-151° C.

IR (1% in KBr): 1735 cm$^{-1}$ (C=O stretching).

$^1$H-NMR (CDCl$_3$, 300 MHz) δ(ppm): 6.97 (m, 2H); 7.34 (d, AA' portion of AA'BB' system, 2H, $J_{H-H}$=8.6 Hz); 7.44 (ddd, 1H, $J_{H-H}$=6.34 Hz, $J_{H-F}$=8.6 Hz, $J_{H-F}$=8.6 Hz); 7.61 (dd, BB' portion of AA'BB' system, 2H, $J_{H-H}$=8.6 Hz, $J_{H-F}$=1.6 Hz); 8.39 (d, AA' portion of AA'BB' system, 2H, $J_{H-H}$=9.0 Hz); 8.39 (d, AA' portion of AA'BB' system, 2H, $J_{H-H}$=9.0 Hz); 8.43 (d, BB' portion of AA'BB' system, 2H, $J_{H-H}$=9.0 Hz).

$^{19}$F-NMR (CDCl$_3$, 283.2 MHz) δ(ppm): −107.75 (m, 1F); −105.15 (m, 1F).

EXAMPLE 4

Preparation of compound V Compound IV (1 g; 2.9 mmoles) was dissolved in methylene chloride (5 ml) under nitrogen and the solution was heated at 40° C.

m. Chloroperbenzoic acid (1.53 g; 89.6% titre; 8.8 mmoles) was added under stirring in one portion to the reaction mixture. The mixture was heated under reflux for 45 hours under stirring and under nitrogen.

Ethyl ether (10 ml) was added to the mixture cooled at 25° C. After filtration and evaporation of the solvent under reduced pressure a residue, containing ester V and ketone IV in the ratio 96:4 from HPLC analysis, was obtained (93.5% yield).

EXAMPLE 5

Preparation of compound V

Compound IV (3 g; 8.8 mmoles), methylene chloride (10 ml), maleic anhydride (5.09 g) and methanesulfonic acid (2.55 g; 26.5 mmoles) were mixed under nitrogen. The reaction mixture was heated at 53° C. (external temperature) under stirring up to complete dissolution. Hydrogen peroxide at 57.8% (1.12 g; 19.1 mmoles) was added in 3 hours at 53° C. After 30 minutes from the end of the addition, the reaction mixture was diluted with methylene chloride (20 ml) and poured into water (20 ml). The organic phase was washed with water (20 ml), dried and the solvent was evaporated to dryness. A crude containing ester V (85% yield) was obtained.

EXAMPLE 6

Preparation of 4-(2,4-difluorophenyl)-phenol (compound III)

A suspension of compound V (0.7 g) in 10% aqueous sodium hydroxide (2 ml) was heated under reflux under stirring for 1 hour.

After cooling at room temperature, the reaction mixture was acidified with concentrated HCl and extracted with ethyl ether (10 ml). The ethereal solution was washed with an 8% sodium bicarbonate solution (10 ml) and evaporated to dryness giving compound III (0.406 g; 100% yield).

m.p. 152°-154° C.

What we claim is:

1. A process for the preparation of 4-(2,4-difluorophenyl)-phenyl 4-nitro-benzoate comprising the Friedel-Crafts acylation of 2,4-difluorobiphenyl with 4-nitro-benzoyl chloride in order to obtain 4-(2,4-difluorophenyl)-4'-nitro-benzophenone and the Baeyer-Villiger oxidation of this latter.

2. 4-(2,4-difluorophenyl)-phenyl 4-nitro-benzoate.

* * * * *